Figure 1:
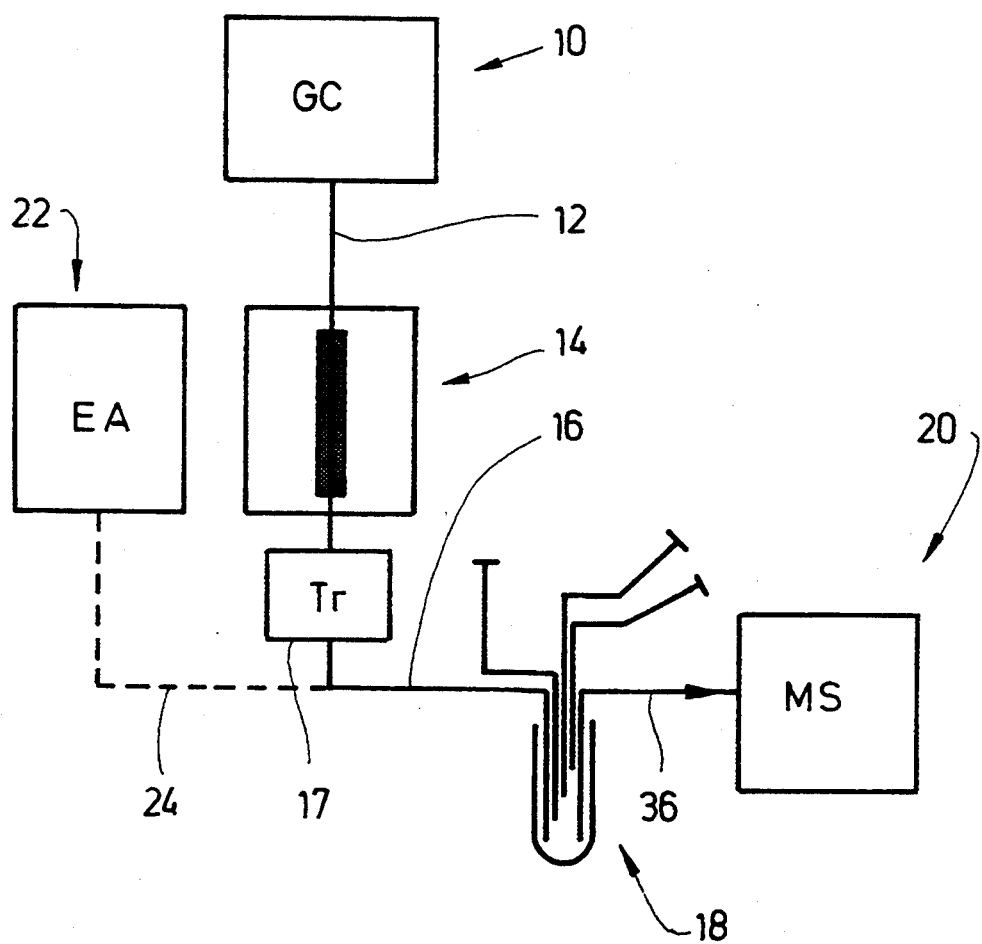

United States Patent [19]
Brand et al.

[11] Patent Number: 5,424,539
[45] Date of Patent: Jun. 13, 1995

[54] PROCESS FOR THE ANALYSIS OF GASEOUS COMPONENTS BY MASS SPECTROMETRY

[75] Inventors: Willi Brand, Stuhr; Karleugen Habfast, Bremen, both of Germany

[73] Assignee: Finnegan Mat GmbH, Bremen, Germany

[21] Appl. No.: 167,537

[22] Filed: Dec. 14, 1993

[30] Foreign Application Priority Data

Dec. 18, 1992 [DE] Germany .................. 42 42 860.2
Jan. 19, 1993 [DE] Germany .................. 43 01 225.6
Sep. 29, 1993 [DE] Germany .................. 43 33 208.0

[51] Int. Cl.$^6$ .................................................. H01J 49/04
[52] U.S. Cl. .................................... 250/288; 250/282
[58] Field of Search ............... 250/288, 288 A, 282; 436/161, 173; 422/320; 73/23.37

[56] References Cited

U.S. PATENT DOCUMENTS

| | | | |
|---|---|---|---|
| 4,641,541 | 2/1987 | Sharp | 250/288 A |
| 4,654,052 | 3/1987 | Sharp | 55/67 |
| 4,705,669 | 11/1987 | Tsuji et al. | 422/93 |
| 4,866,270 | 9/1989 | Hall et al. | 250/288 A |
| 4,916,313 | 4/1990 | Hall et al. | 250/288 A |
| 4,988,870 | 1/1991 | Diehl | 250/288 |
| 5,012,052 | 4/1991 | Hayes | 250/288 |
| 5,281,397 | 1/1994 | Ligon et al. | 250/288 A |

OTHER PUBLICATIONS

European patent application No. A2 0 032 984 filed Nov. 20, 1980.
Article entitled "A Versatile Interface Modification for GC/MS on Benchtop Instruments", by L. Hathcock, Q. W. Zhang, and W. Bertsch, from Journal of High Resolution Chromatography, vol. 13 Sep. 1990, p. 656.
Article entitled "Techniques for Postcolumn Derivatization in Gas Chromatography/Mass Spectrometry", by Woodfin V. Ligon, Jr. and Hans Grade, from Anal. Chem. 1991, 63, pp. 255–261.
Article entitled "Open Split Interface for Capillary Gas Chromatography/Mass Spectrometry", by R. F. Arrendale, R. F. Severson and O. T. Chortyk, from Anal. Chem. 1984, 56, pp. 1533–1537.
Article entitled "Isotope-Ratio-Monitoring Gas Chromatography–Mass Spectrometry" by D. E. Matthews and J. M. Hayes, from Analytical Chemistry, vol. 50, No. 11, Sep. 1978, pp. 1465–1473.
Article entitled "Compound-specific isotopic analyses: A novel tool for reconstruction of ancient biogeochemical process". by J. M. Hayes, Katherine H. Freeman, Brian N. Popp and Christopher H. Hoham, from Advances in Organic Geochemistry 1989, vol. 16, Nos. 4–6, pp. 1115–1129, 1990.

*Primary Examiner*—Jack I. Berman
*Assistant Examiner*—James Beyer
*Attorney, Agent, or Firm*—Flehr, Hohbach, Test, Albritton & Herbert

[57] ABSTRACT

Background of the invention is the isotope ratio analysis of carbon and nitrogen as components of hydrocarbon compounds. The separation into individual components takes place in a gas chromatograph and oxydation in a downstream combustion oven, into, inter alia $CO_2$ and $N_2$. In general $CO_2$ is present in a much larger quantity than $N_2$. The measurement values on the mass spectrometer have accordingly different dimensions. In order to approximate the peak values, a dilution with additional helium as a carrier gas takes place in the analysis of $CO_2$. This has the additional advantage that the helium as a carrier gas, which is present anyway, as a result is present in approximately equal quantities relative to the $CO_2$ and $N_2$ in the ion source of the mass spectrometer. The dilution takes place in the region of a so-called open split (18).

10 Claims, 4 Drawing Sheets

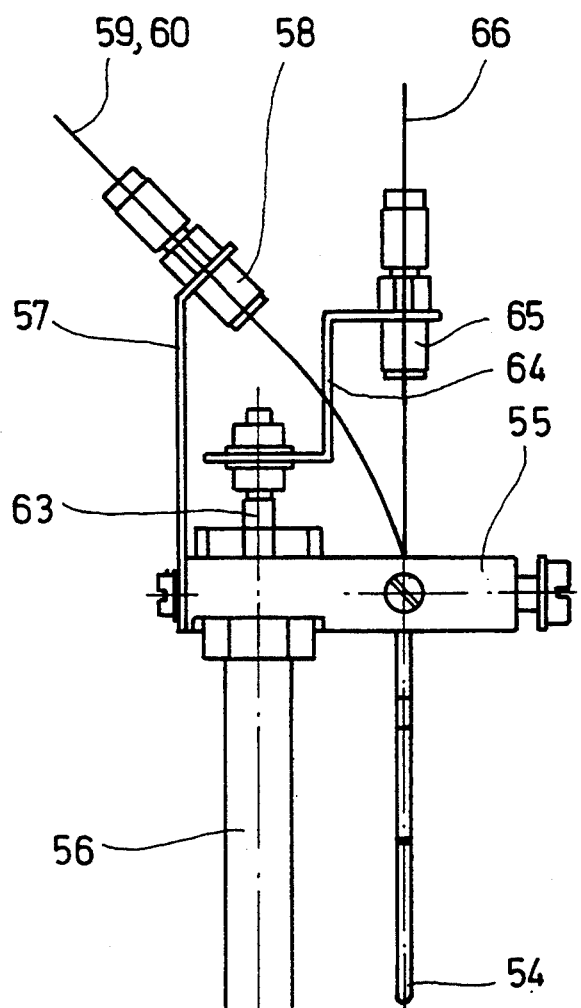
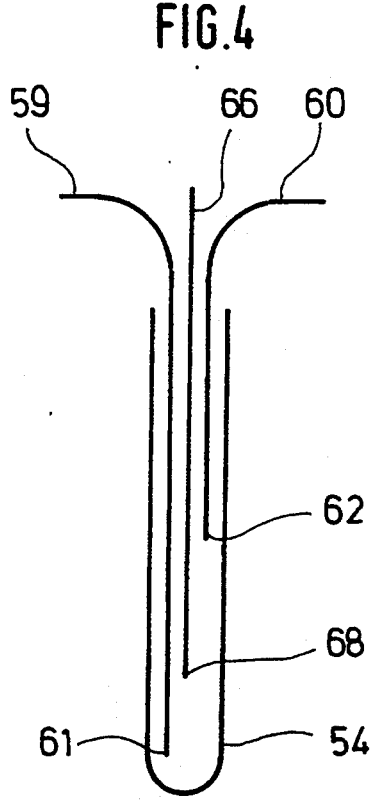
FIG.3
FIG.4

PROCESS FOR THE ANALYSIS OF GASEOUS COMPONENTS BY MASS SPECTROMETRY

The invention relates to a process for the analysis of several, especially two, gaseous components by mass spectrometry, the components being supplied, simultaneously or successively, with a carrier gas to a mass spectrometer, the first component having a different volume ratio relative to the carrier gas compared to the second component. Furthermore, the invention relates to an apparatus for the provision of gaseous samples for an analysis by mass spectrometry, especially for conducting the process.

Background of the invention and its preferred field of application is the isotope-ratio analysis by mass spectrometry, especially of carbon and nitrogen or, for example, of sulphur. In the course of a so-called GC-IRMS-analysis, for example, organic compounds or compound mixtures can be separated in a gas chromatograph (GC) and the separated components can be decomposed in a downstream combustion oven. If the organic compound or the compound mixture contains carbon, hydrogen and nitrogen, $CO_2$, $H_2O$ and $N_2$ are formed in the combustion oven by oxidation. In this case, it is relevant to determine the isotope ratios $C12/C13$ of the $CO_2$ and $N14/N15$ of the $N_2$. This is attained by means of the downstream mass spectrometer, the sample gases $CO_2$ and $N_2$ being allowed to flow in on-line into the ion source of the mass spectrometer. The principle of the method is described, for example, in Analytical Chemistry, Vol. 50, Nr. 11, September 1978, pages 1465-1473 and in Org. Chem., Vol 16, Nr. 5-6, pages 1115-1128. Sometimes this analytical method is also abbreviated IRM-GCMS. Utmost precision is required in such analyses. In order to attain the required precision, the sample gases ($CO_2$ and $N_2$) are allowed to reciprocally flow into the mass spectrometer with a standard gas of which the isotope ratio is known. In the measurements, only the deviation of the isotope ratio of the sample relative to the standards is important. The deviations may be extremely small.

During a measurement, alternately $CO_2$ or $N_2$ and corresponding reference gases, i.e. $CO_2$ and $N_2$ having a standard isotope ratio, are supplied to the mass spectrometer. Normally, the quantity of $CO_2$ produced in the analysis of organic compounds is much higher than the quantity of $N_2$ (20:1 to 50:1). If the gases were allowed to flow into the MS in this ratio of concentration, ion currents of very different sizes would be generated for $CO_2$ and $N_2$. A mass spectrometer, however, operates at its optimum only in a certain range of ion current. It is, therefore, expedient to adjust the ion currents to one another. This can not be achieved by simply reducing the gas inflow of $CO_2$, for example by means of a throttle valve. A change in the throttling of the gas inflow always causes a change (even if only a small one) of the isotope ratio (fractionation). A further problem arises: carrier gas (preferably helium) flows into the mass spectrometer together with the sample gas. The concentration of the carrier gas is substantially higher than that of the sample gas. This carrier gas is ionized in the ion source of the mass spectrometer together with the sample gas and produces a relatively high volume charge. As a change in the throttling of the gas inflow equally affects sample gas and carrier gas, the volume charge would be changed thereby. The volume charge, however, influences the ion-optical properties of the mass spectrometer (focusing of the ions) and, therefore, has to be held constant in precision measurements of isotope ratios. This is another reason why a change of the gas inflow would be very inappropriate.

The object of the present invention is to create a process or an apparatus which allows an isotope-ratio anylsis which as precise as possible.

The process according to the invention is characterized in that, in the analysis of a component which has the greater concentration with respect to the carrier gas, the concentration of this component is reduced by supplying additional carrier gas. Accordingly, in the analysis of $CO_2$ in connection with helium as a carrier gas, the sample gas is diluted with additional helium. Thereby, the concentrations of the sample gases in the carrier gas can be approximated to one another, so that the negative effects different concentrations of the sample gases have on the precision of measurement can be avoided. The total gas inflow is practically not affected by the addition of helium, because it is determined exclusively by the throttling effect of the inflow capillaries in the mass spectrometer. If the sample or component to be analyzed contains $CO_2$ and $N_2$, succesive measurements are conducted in the mass spectrometer, for example a determination of the isotope ratio of the $N_2$ first, and a subsequent measurement of the $CO_2$. Each measurement is compared to the standard samples.

Known per se is the principle of an open split before the entry of the gases to be analyzed in the ion source of the mass spectrometer. A fraction of the gases emerging from a line is transferred almost under atmospheric pressure to a further line. The largest portion of the gases to be analyzed is discharged as excess and thereby displaces possible secondary air flows. Advantageously, the dilution with additional carrier gas takes place in the region of this open split. The additional carrier gas does not influence the pressure ratio and flow conditions. Merely the ratio of carrier gas and gas to be analyzed is changed, especially of helium and $CO_2$.

The dilution appropriately takes place in such a manner that the concentrations of the gases to be analyzed ($CO_2$ or $N_2$) become approximately equal. To be more specific, after dilution the quantity of $CO_2$ in the $CO_2$-analysis corresponds to the quantity of $N_2$ in the $N_2$-analysis. For this reason the isotope-ratio analysis can be carried out with very high precision.

Starting out from an apparatus according to the preamble of the independent apparatus claim, the apparatus according to the invention is characterized in that a further supply line (dilution line) is provided, via which a further gas, in addition to the other gases emerging from the other supply lines, can be supplied to the throttle line. This apparatus makes it possible to carry out the above-mentioned process.

Figure 2:
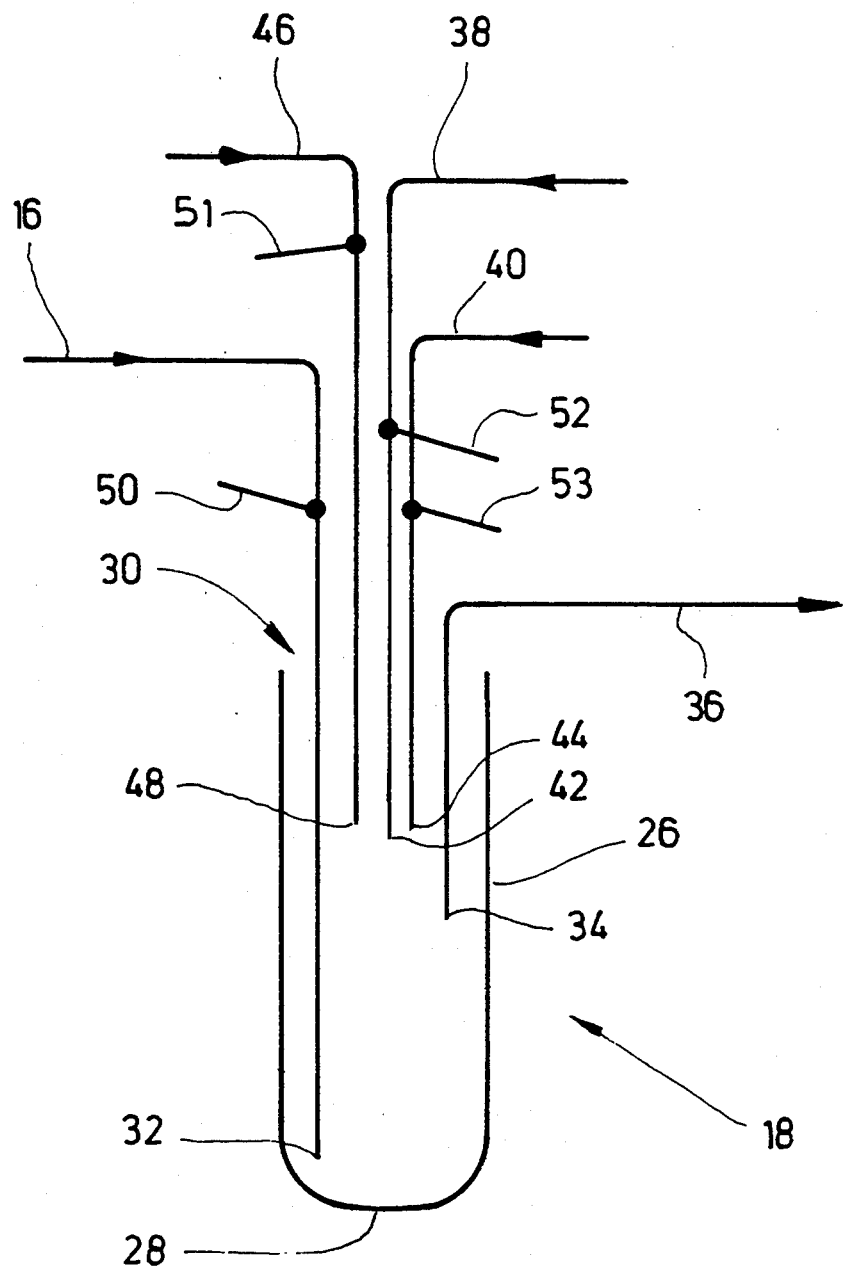
Figure 5:
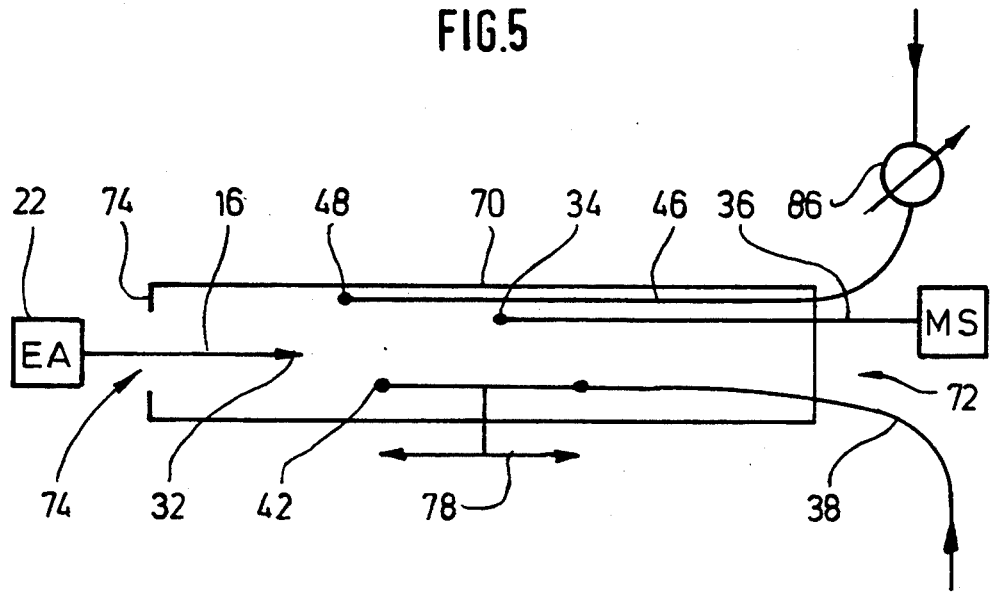
Figure 6:
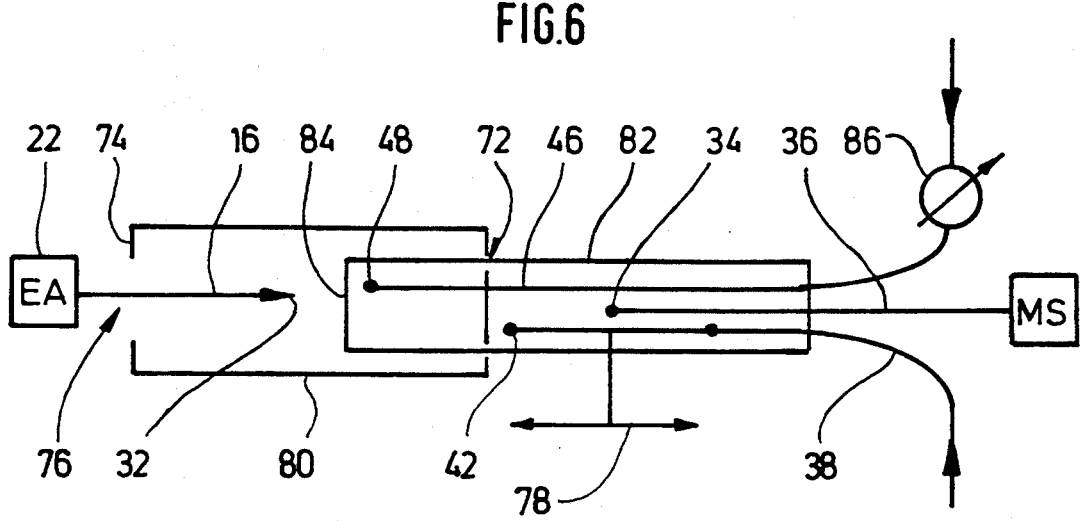

Further features of the invention are to be found in the subclaims and the description. Exemplary embodiments of the invention are explained in detail hereinafter by means of the drawings. In these:

FIG. 1 shows a diagrammatic representation of a system for conducting an isotope-ratio analysis, FIG. 2 shows an enlarged detail of FIG. 1, namely a so-called open split in an embodiment according to the invention, FIG. 3 shows an open split for the demonstration of the movement of the capillaries, FIG. 4 shows the basic structure of the open split according to FIG. 3, FIG. 5 shows a further embodiment of an open split in a representation similar to FIG. 2, FIG. 6 shows a variation in a representation similar to FIG. 5.

The system shown in FIG. 1 is provided for conducting an isotope-ratio analyses by mass spectrometry. Two different embodiments are explained by means of the same figure. The point of departure is a gas chromatograph 10 (GC). A component of the sample contained therein and separated from the other components, for example an amino acid, is supplied to a combustion oven 14 via a line 12 and is oxidated therein. The combustion products resulting therefrom are separated in time via a gas supply line 16 in a second gas chromatograph 17 designated "Tr" for the separator in FIG. 1. Finally, the combustion products are supplied to a so-called open coupling (open split) 18 of the ion source of a mass spectrometer 20 (MS) comprising a multiple collector. For the analysis of $CO_2$, for example a double collector can be employed, that is to say one collector each for the ions with the mass number 44 (C12) and 45 (C13), respectively. This type of analysis—without the second gas chromatograph 17—is known as IRM-GCMS (Isotope-Ratio-Monitoring Gas-chromatography-Mass Spectrometry) or as GC-IRMS (Gas-chromatography Isotope Ratio Mass Spectrometry). Corresponding to the schematic representation in FIG. 1, further details necessary for the analysis, for example valves or additional supply lines, are not shown if they are not in directly related to the invention.

In another, very important application, a so-called element analyzer (EA) 22 or CHN-analyzer is employed instead of structural components 10, 12, 14, 17. A combustion oven and a GC are integrated in the E A. For example solid samples are fed into the EA and burned therein. Gases which are formed during combustion are separated in time, emerge one after another and thus can be fed one after another, via a supply line 24, to the line 16 which is connected to the open split 18.

The open split 18 is shown in more detail in FIG. 2 and takes the form of a small coupling tube 26 open at one side with a closed bottom 28 and an open end face 30. The gas emerging from the gas chromatograph or the combustion oven is piped into the region of the bottom 28 via a supply line 16 with a corresponding opening 32. The gas is discharged via an opening 34 of a snifting or throttling line 36 which leads to the mass spectrometer, said opening 34 being located approximately centrally relative to the height of the small tube 26 (above the opening 32). The object is to determine the isotope ratios for carbon and nitrogen in the gases $CO_2$ and $N_2$ contained in one or various samples. Accordingly, two supply lines 38, 40 are provided for reference samples with exactly defined isotope ratios of the mentioned gases. Openings 42, 44 of the supply lines 38, 40 also end inside of the small coupling tube 26.

In connection with the invention particular emphasis is given to a further supply line, namely a dilution line, which has an opening 48 that ends in the small coupling tube 26. Additional carrier gas can be supplied by this small coupling tube 26.

For controlling the gas inlet into the opening 34 by varying immersion of the lines 46, 38 and/or 40, said lines are axially moveable. A mechanical device provided for this purpose is outlined by appropriate levers 51, 52, 53 in FIG. 2. These can be operated separately or in groups, so that the corresponding openings 48, 42, 44 are variable in their distance to the opening 34 of the inlet capillaries (snifting line 36). In an idle position, the lines 38, 40, 46 rest above the snifting line 36 until they are needed.

The above system serves for a successive analysis of $N_2$ and $CO_2$. Thus, a gas sample containing $N_2$ and $CO_2$, for example, is supplied together with helium as a carrier gas in a volumetric rate of flow of 60 ml/min via the line 16 in the position according to FIG. 2. The small coupling tube 26 has an inner diameter of approximately 1 mm. The portions of the lines 16, 46, 38, 40, 36 which are inside the small coupling tube 26 are designed as capillaries in a correspondingly fine manner. The volume of the gas entering into the small coupling tube 26 via the opening 32 is such that all secondary air is displaced from the region of the bottom 28. Furthermore, gas which possibly emerges from the openings 48, 42, 44 in the position shown in FIG. 2 does not reach the bottom area. Thus, the gas flowing into the opening 34 of the throttling line 36 is always only a fraction of the gas coming from the line 16. The throttling line 36 has a precisely defined cross-section so that under constant compression ratios a constant gas supply to the mass spectrometer is ensured.

At times, a reversal of the lines takes place in order to supply a reference gas. For example a nitrogen gas $N_2$ with a known standardized isotope ratio can be supplied via line 40. This is done by lowering the line 40 by operating lever 53. As a result the opening 44 is located underneath the opening 34 so that the throttling line 36 is supplied with a mixture of reference gas and helium. Expediently, this operation takes place in an interval in which no sample gas emerges from the opening 32 or in which the line 16 is pulled out up to a level above the opening 34. The alternation between the sample gas via the line 16 and the reference gas via the line 40 is repeated several times.

After the measurement of the nitrogen gas $N_2$, the measurement of carbon dioxide takes place. As before, the sample gas flows into the small coupling tube 26 via the line 16 similar to the above-described procedure. The introduction of a reference gas via the line 38 is carried out in the above-described manner by means of an appropriate lever 52 ($CO_2$ with standard isotope ratio and helium as carrier gas) as well. The mass spectrometer is, accordingly, readjusted from the masses for nitrogen isotopes to the masses of carbon isotopes.

The reading of the mass spectrometer 20 depends on the number of ions of the supplied sample gas. In the analysis of organic compounds or compound mixtures normally much more $CO_2$ is produced for the analysis than $N_2$, and supplied with helium as carrier gas to the mass spectrometer 20 via the open split 18. In other words, the quantity of gas flowing in through the throttling line 36 at first contains a very large proportion of helium, a fraction of $N_2$ and, compared to the latter, a much larger proportion of $CO_2$. In order to attain a very high precision of measurement, the quantity of helium should possibly be equal relative to both gases. At the same time, an adjustment of the maximum $CO_2$ value to the maximum $N_2$ value is advantageous for the evaluation. For this purpose, a dilution with additional carrier gas takes place during the analysis of $CO_2$. For this purpose, a further quantity of helium is introduced into the small coupling tube 26 via the line 46. To control this quantity, the line 46 is axially moveable by means of the lever 51. Each time the opening 48 of the capillaries 46 (line) immerses into the space underneath the opening 34 of the snifting capillaries 36, the sample gas emerging from the opening 32 is diluted with carrier gas. The gas which is passed into the capillaries and into the mass spectrometer via the opening 34 is thereby diluted until the proportion of helium relative to the $CO_2$ is approximately equal to the proportion of helium as it was before relative to the $N_2$.

In a further embodiment, the control of the gas supply is attained, in addition to or instead of the variation of the depth of immersion of the individual lines by means of the levers 51 to 53, by a limitation of the gas flow in the lines themselves, for example by means of appropriate valves. The switching over from the sample gas in the analysis of $N_2$ to a corresponding reference gas $N_2$ can thus take place by throttling the line 16 and opening the line 40. Both lines should end in the area of the bottom 28. Similarly, switching over to a reference gas $CO_2$ in the analysis of $CO_2$ can take place by throttling the line 16 and opening the line 38, also with openings 32, 42 in the region of the bottom 28. Additionally, in this case, it is necessary to control the gas for dilution by turning on the line 46 or deeply immersing the line 46 when it is open.

An example for carrying out the movement of lines inside of a small coupling tube will be explained below by means of FIGS. 3 and 4. A small coupling tube referred to as pipette 54 (corresponding to the small coupling tube 26), is fixed to a stand 55. Also fixedly connected thereto is a cylinder 56 of a piston-cylinder unit as well as a retaining plate 57. The latter carries a support 58 for the accomodation of two capillaries 59, 60 (lines). These capillaries both reach into the pipette 54 with corresponding openings 61, 62.

A piston 63 which can be drawn out of the piston-cylinder unit (cylinder 56) carries a retaining plate 64. A support 65 is fixed thereto for the accomodation of a further capillary 66. The piston is vertically adjustable by admitting compressed air to the piston-cylinder unit (flexible tube connection 67). Accordingly, the capillary 66 is moved up or down in the pipette.

For the sake of clarity, only one moveable capillary 66 is shown in FIGS. 3, 4. According to the invention, more than one capillary may be provided. For this purpose the capillaries may immerse into the pipette 54 in curved shape, corresponding to the capillaries 59, 60. For example so-called fused silicia capillaries are both flexible and axially moveable.

In the example shown in FIGS. 3 and 4, the capillary 59 with an inner diameter of 0.1 mm is provided for the introduction of helium, if necessary in connection with a sample gas. The capillary 66 has an inner diameter of 0.05 mm and is provided for the introduction of a reference gas. The capillary 66 ends in an opening 68 in an adjustable region, preferably between the openings 61, 62. Finally, the capillary 60 is provided as a snifting line, that is to say as a line with an inner diameter of 0.05 mm which leads to the mass spectrometer.

In the present example, a pneumatic actuation is provided for the movement of the capillaries 66. Other actuations, for example electrical or hydraulic, are possible.

FIGS. 5 and 6 relate to further embodiments of the invention. FIG. 5 shows a modification compared to FIG. 2, comprising a small coupling tube 70 which is open at both ends. The gas supply line 16, dilution line 46, throttling line 36 as well as the reference gas line 38 correspond to the lines shown in FIG. 2. Just as in FIG. 2, further lines may be provided the embodiment according to FIG. 5, for example a further reference gas line. The small coupling tube 70 is open at an end face 72. The lines 46, 36, 38 immerse on this side (dilution line, throttling line, supply line). The opposite end face 74 is partly closed or has only a comparatively smaller inlet cross-section 76. The gas supply line 16 coming from the element analyzer 22 enters the small coupling tube 70 via the decreased inlet cross-section 76. Similar to FIG. 1, a supply from a gas chromatograph with downstream combustion oven and separating device may also occur.

A control of the gas concentration entering the opening 34 of the throttling line 36 is possible by longitudinal displacement of the individual lines, especially 16, 38 and 46. Alternatively or additionally, the gas flows in the individual lines can be throttled or shut off. According to the embodiment of FIG. 5, an axial movability of the reference gas supply line 38 is preferred. The movability is indicated by a double arrow 78. In the position shown in the figure, the reference gas moves from the dilution line 46 to the throttling line 36, if necessary, together with a gas volume. If the reference gas supply line 38 is moved to the right, pratically no reference gas reaches the throttling line 36.

FIG. 6 shows an expanded embodiment compared to FIG. 5. Instead of one small coupling tube 70, according to FIG. 6, two small coupling tubes are provided, in particular a thicker small coupling tube 80 and a thinner small coupling tube 82, which enters the former. The latter is open at both ends. The small coupling tube 80 corresponds in its structure to the small coupling tube 70, but is thicker in diameter. The inner diameters of the small coupling tubes 80, 82 are approximately 3 mm and 0.7 mm, respectively. Accordingly, the gas flow emerging from the opening 32 splits in the ratio of the end faces of the tubes (approximately 8.5:0.5). The small coupling tube 80 thus has the function of a precoupling towards the small coupling tube 82. The reference gas and the additional helium carrier gas enter the small coupling tube 82 via the lines 38 and 46, are mixed in the small coupling tube 82 and then enter the throttling line 36. Only opening 32 is located in the thicker small coupling tube 80.

A particular advantage of this embodiment is the uncoupling of the reference gas supply from the gas supply via the line 16 (sample supply). If different quantities of $CO_2$ (or other gases) are supplied at different times, the cross-section of the line 38 is best only for a certain volumetric rate of flow. Without the described coupling of the two small tubes 80, 82, the line 38 would have to be replaced with another line with appropriate diameter each time. In the embodiment according to FIG. 6, surplus reference gas can emerge via the coupling between the two small tubes 80, 82. Moreover, there are further advantages. Under normal operation, according to the description of FIGS. 1 to 5, significantly reduced consumptions of the reference gas and the auxiliary helium flow (line 46) can be attained. For controlling the reference gas supply, the volumetric flow rate is variably adjustable by means of the line 46, preferably between 0 and 20 ml/min. The opening 48 is located closely in front of the end 84 of the small tube 82 which is located inside of the small tube 80. The opening 34 is located approximately centrally in the small tube 82. A very small volumetric flow rate from the opening 48 already causes a partial displacement of the sample gas emerging from the opening 32. The latter does not enter into the small tube 82, but, on the contrary, exits via the end face 72. As a result a dilution of the sample gas can be attained with significantly reduced carrier gas supply.

Just like in the embodiment according to FIGS. 1 to 4, axial movements of the lines would be possible in this embodiment by levers not shown.

Approximately a third or one half of the thinner coupling tube 82 is located within the thicker small tube 80. The opening 32 is located at a distance in front of the end 84. The dimensions of the thinner small tube 82 correspond to those of the small tube 70 or 54. The small tube 80 has approximately the same length but is substantially thicker. A throttle valve in the tubing 46 is designated by the reference numeral 86.

The small tubes 70, 80, 82 and the capillaries (lines 36, 38, 46, 16) can be fixed and moved just as shown in the representation in FIG. 3.

Organic compounds may contain further elements in addition to carbon and nitrogen, for example sulphur. In this case, gaseous $SO_2$ would result from the combustion. The corresponding isotope ratio can be determined in the described manner, just as the isotope ratios of further elements.

We claim:

1. Process for the analysis of first and second different gaseous components by mass spectrometry, the components being supplied in succession, with a carrier gas to a mass spectrometer, the first component having a different volume ratio relative to the carrier gas compared to the second component, characterized in that, in the analysis of a component which is provided in a greater ratio relative to the carrier gas, the concentration of such component is decreased or diluted by additional supply of carrier gas.

2. Process according to claim 1, characterized in that the dilution with additional carrier gas is carried out in the region of an open split (18).

3. Process according to claim 1, characterized in that the dilution with carrier gas continues until the concentrations of the gases to be analyzed become approximately equal.

4. Apparatus for the provision of gaseous samples for the analysis by mass spectrometry comprising an open split (18), at least one sample supply line (16), at least one reference gas supply line (38, 40) and a throttling line (36) which leads from the open split to the ion source of a mass spectrometer (20), where the gas can be fed to the throttling line (36) alternately from one of the supply lines (16, 38, 40) approximately under atmospheric pressure, characterized in that a further supply line (146) is provided in said split, via which a further gas can be fed to the throttling line (36) in addition to the gas emerging from one of the other supply lines (16, 38, 40) for dilution.

5. Apparatus according to claim 4, characterized in that, in the region of the open split (18), an outlet opening (32) of the gas sample supply line (16) is disposed adjacent to an inlet opening (34) of the throttling line (36), and that in the region near the inlet opening (34) the dilution line (46) with its outlet opening (48) can be moved in an out relative to said open split.

6. Apparatus according to claim 4 characterized in that the reference gas supply lines (38, 40) can each be moved in and out relative to said open split.

7. Apparatus according to claim 4 characterized in that the open split (18) takes the form of a coupling tube (26) open at one end, into which the lines (16, 46, 38, 40) are inserted as capillaries from at least one open end face (30).

8. Apparatus according to claim 7, characterized in that the capillaries of the dilution line (46) and the reference gas lines (38, 40) are moveable in the longitudinal direction of the coupling tube (26) and inside of same.

9. Apparatus according claim 4 characterized by the following features:
   a) the open split has two coupling tubes (80, 82),
   b) a portion of one of said coupling tubes (82) is inserted in the other said coupling tube (80),
   c) at least the throttling line (36), the dilution line (46) and the reference gas supply line (38) end in said one coupling tube (82),
   d) the supply line (16), from which the sample gases to be analyzed emerge, ends in said other coupling tube (80),
   e) the cross-sectional surface of said other coupling tube (80) is substantially greater than, substantially 10–20 times the cross-section of said one coupling tube (82), so that the surplus gas volume from the one tube (82) can emerge from the open split via the end face (72) of the other tube (80).

10. Process according to claim 2, characterized in that said dilution is carried out with an almost pressureless transfer of a gas emerging from one line in said split to another line in said split, a part of the gas emerging from said one line being discharged as surplus from said split.

* * * * *